(12) United States Patent
Alkhowaildi et al.

(10) Patent No.: US 10,889,752 B2
(45) Date of Patent: Jan. 12, 2021

(54) FOAMING MIXTURES AND METHODS OF USE THEREOF

(71) Applicant: Saudi Arabian Oil Company, Dhahran (SA)

(72) Inventors: Mustafa Alkhowaildi, Safwa (SA); Zuhair Yousef, Saihat (SA); Sunil Kokal, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1 day.

(21) Appl. No.: 16/267,871

(22) Filed: Feb. 5, 2019

(65) Prior Publication Data

US 2020/0248065 A1  Aug. 6, 2020

(51) Int. Cl.
C09K 8/594 (2006.01)
C09K 8/584 (2006.01)
E21B 43/16 (2006.01)

(52) U.S. Cl.
CPC .............. *C09K 8/594* (2013.01); *C09K 8/584* (2013.01); *E21B 43/16* (2013.01); *E21B 43/164* (2013.01)

(58) Field of Classification Search
None
See application file for complete search history.

(56) References Cited

U.S. PATENT DOCUMENTS 5,750,584 A   5/1998  Knaus
7,939,471 B2  5/2011  Welton et al.
2008/0015271 A1  1/2008  Abram et al.
2008/0161212 A1  7/2008  Welton et al.
2009/0159288 A1  6/2009  Horvath Szabo et al.
2010/0071957 A1*  3/2010  Huang ................... C09K 8/524
175/65

(Continued)

FOREIGN PATENT DOCUMENTS

CN   108347920 A   7/2018
EP       555690 A1   8/1993
EP      3023476 A1   5/2016

(Continued)

OTHER PUBLICATIONS

U.S. Department of Energy, "Carbon Dioxide Enhanced Oil Recovery, Untapped Domestic Energy Supply and Long Term Carbon Storage Solution", Nation Energy Technology Laboratory.

(Continued)

*Primary Examiner* — Andrew Sue-Ako
(74) *Attorney, Agent, or Firm* — Dinsmore & Shohl LLP

(57) ABSTRACT

Fluids injected into a carbonate reservoir formation during Enhanced Oil Recovery (EOR) may include a foaming mixture that includes a zwitterionic surfactant, an omega-3-acid ethyl ester, and aqueous salt solution. The omega-3-acid ethyl ester may include eicosapentaenoic acid ethyl ester, docosahexaenoic acid ethyl ester, or combinations thereof. The foaming mixtures may be incorporated into methods for enhancing hydrocarbon recovery in a carbonate reservoir formation. The methods may include introducing the foaming mixture to the carbonate reservoir formation such that any hydrocarbon present in the carbonate reservoir formation is displaced by the foaming mixture and is recoverable from the carbonate reservoir formation.

13 Claims, 1 Drawing Sheet

(56) References Cited

U.S. PATENT DOCUMENTS

2010/0236137 A1* 9/2010 Wu .................. A01K 61/85
 44/385
2016/0346242 A1 12/2016 Brito De La Fuente et al.

FOREIGN PATENT DOCUMENTS

WO  2013184116 A1  12/2013
WO  2015113986 A1   8/2015

OTHER PUBLICATIONS

Schlumberger, "Well Intervention Catalog", vols. 1, 2 & 3 2015.
International Search Report and Written Opinion pertaining to International Application No. PCT/US2019/065986 dated Mar. 16, 2020, 38 pages.

* cited by examiner

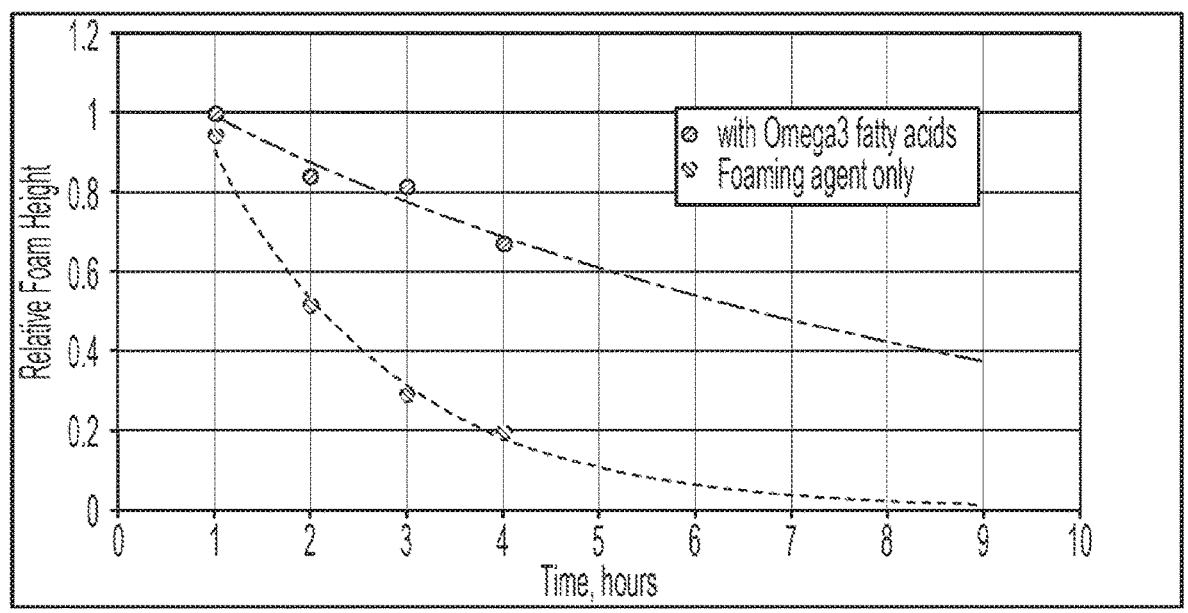

FOAMING MIXTURES AND METHODS OF USE THEREOF

TECHNICAL FIELD

The present specification generally relates to foaming mixtures that enhance hydrocarbon recovery in a carbonate reservoir formation.

BACKGROUND

It is estimated that nearly 60% of the world's oil and 40% of the world's gas reserves are held in carbonate reservoir formations. The Middle East, for example, is dominated by carbonate reservoir formations, with around 70% of oil and 90% of gas reserves held in carbonate reservoir formations. One method of recovering hydrocarbons from carbonate reservoir formations includes enhanced oil recovery (EOR). EOR is a stage of hydrocarbon production that involves methods to recover more oil than would be possible by utilizing only primary production or waterflooding. EOR encompasses a range of techniques used to restore carbonate reservoir formation pressure and improve hydrocarbon displacement or fluid flow in the reservoir. One such EOR technique involves foam flooding, a process in which foaming agents are injected into a reservoir to improve the viscosity of a driving fluid, thereby enhancing the hydrocarbon recovery in carbonate reservoir formations. These foaming agents must be able to withstand a salinity of greater than 57,670 ppm, hard water, solids, entrained oil, and temperatures associated with carbonate reservoir formations. However, foaming agents used in EOR typically include nonionic surfactants, which may not be able to achieve the necessary viscosity and stability properties needed in such harsh environments. As such, the typical foaming agents that include nonionic surfactants may lead to decreased levels of hydrocarbon recovery from carbonate reservoir formations during EOR.

SUMMARY

Accordingly, there are ongoing needs for foaming mixtures that enhance volumetric sweep efficiency during EOR. Embodiments of the present disclosure are directed to foaming mixtures which meet this need by exhibiting increased viscosity and stability in carbonate reservoir formations during EOR compared to typical foaming agents.

According to embodiments of the disclosure, a foaming mixture may include a zwitterionic surfactant, an omega-3-acid ethyl ester, and aqueous salt solution. In some embodiments, the omega-3-acid ethyl ester may comprise eicosapentaenoic acid ethyl ester, docosahexaenoic acid ethyl ester, or combinations thereof.

According to other embodiments of this disclosure, a method for enhancing hydrocarbon recovery in a carbonate reservoir formation includes introducing a foaming mixture to the carbonate reservoir formation such that any hydrocarbon present in the carbonate reservoir formation is displaced by the foaming mixture and is recoverable from the carbonate reservoir formation. The foaming mixture may comprise a zwitterionic surfactant, an omega-3-acid ethyl ester, and aqueous salt solution; and the omega-3-acid ethyl ester is selected from the group comprising eicosapentaenoic acid ethyl ester, docosahexaenoic acid ethyl ester, or combinations thereof.

Additional features and advantages of the embodiments described in this application will be set forth in the detailed description which follows, and in part will be readily apparent to those skilled in the art from that description or recognized by practicing the embodiments described in this application, including the detailed description which follows, the claims, as well as the appended drawing.

It is to be understood that both the foregoing general description and the following detailed description describe various embodiments and are intended to provide an overview or framework for understanding the nature and character of the claimed subject matter. The accompanying drawing is included to provide a further understanding of the various embodiments, and is incorporated into and constitutes a part of this specification. The drawing illustrates the various embodiments described in this application and together with the description serve to explain the principles and operations of the claimed subject matter.

BRIEF DESCRIPTION OF THE DRAWINGS

FIG. 1 is a graph of the height of the foaming mixture over time, according to one or more embodiments presently described.

DETAILED DESCRIPTION

Recitations in the present disclosure of "at least one" component, element, constituent, compound, or other feature, should not be used to create an inference that the alternative use of the articles "a" or "an" should be limited to a single component, element, constituent, compound, or feature. For example, "an alcohol" may refer to one alcohol or more than one alcohol.

Aqueous Salt Solution

Accordingly, reference will now be made in detail to embodiments of methods for enhancing hydrocarbon recovery in a carbonate reservoir formation.

According to embodiments of this disclosure, methods are disclosed for enhancing hydrocarbon recovery in a carbonate reservoir formation. The method may include introducing a foaming mixture to the carbonate reservoir formation such that any hydrocarbon present in the carbonate reservoir formation is displaced by the foaming mixture and is recoverable from the carbonate reservoir formation. The foaming mixture may comprise a zwitterionic surfactant, an omega-3-acid ethyl ester, and aqueous salt solution; and the omega-3-acid ethyl ester is selected from the group comprising eicosapentaenoic acid ethyl ester, docosahexaenoic acid ethyl ester, or combinations thereof.

As stated previously, a foaming mixture according to one or more embodiments may comprise a zwitterionic surfactant, an omega-3-acid ethyl ester, and aqueous salt solution, in which the omega-3-acid ethyl ester comprises eicosapentaenoic acid ethyl ester and docosahexaenoic acid ethyl ester. In some embodiments, the foaming mixture is incorporated into a method for enhancing hydrocarbon recovery in a carbonate reservoir formation.

The foaming mixture will now be described in detail. In some embodiments, the zwitterionic surfactant may comprise a zwitterionic alkyl amine. The zwitterionic alkyl amine may be selected from lauramine oxide, cocamine oxide, cocamidopropyl betaine, myristamine oxide, or combinations thereof.

In certain embodiments, the zwitterionic alkyl amine may comprise between 15 percent by weight (wt. %) and 40 wt. % of the zwitterionic surfactant, based on the total weight of the zwitterionic surfactant. Additional suitable ranges of the zwitterionic alkyl amine present in the zwitterionic surfactant may comprise between 17 wt. % and 38 wt. %, between 19 wt. % and 36 wt. %, between 20 wt. % and 35 wt. %, between 22 wt. % and 33 wt. %, between 24 wt. % and 31 wt. %, between 25 wt. % and 30 wt. %, or from any other range between 15 wt. % and 40 wt. %, based on the total weight of the zwitterionic surfactant. In specific embodiments, the amount of the zwitterionic alkyl amine present in the zwitterionic surfactant is about 25 wt. %, based on the total weight of the zwitterionic surfactant.

In some embodiments, the zwitterionic surfactant may further comprise an alcohol. The alcohol may include at least one primary alcohol, at least one secondary alcohol, or combinations thereof. Suitable alcohols may include any primary alcohol or secondary alcohol having between one and six carbon atoms. Specific suitable primary alcohols may include, but are not limited to methanol, ethanol, 1-propanol, n-butanol, 1-pentanol, 1-hexanol, or combinations thereof. Specific suitable secondary alcohols may include, but are not limited to isopropanol, 2-butanol, 2-pentanol, 2-hexanol or combinations thereof. In certain specific embodiments, the alcohol present in the zwitterionic surfactant comprises isopropanol.

Referring still to the zwitterionic surfactant, the alcohol may comprise between 10 wt. % and 30 wt. % of the zwitterionic surfactant, based on the total weight of the zwitterionic surfactant. The balance of the zwitterionic surfactant may comprise aqueous salt solution, embodiments of which are described below. Additional suitable ranges of the amount of alcohol present in the zwitterionic surfactant may range between 12 wt. % and 28 wt. %, between 14 wt. % and 26 wt. %, between 15 wt. % and 25 wt. %, between 16 wt. % and 24 wt. %, between 18 wt. % and 22 wt. %, or any other range between 10 wt. % and 30 wt. %, based on the total weight of the zwitterionic surfactant. In specific embodiments, the amount of alcohol present in the zwitterionic surfactant is about 20 wt. %, based on the total weight of the zwitterionic surfactant.

Referring now to the omega-3-acid ethyl ester, which is present in the foaming mixture. The omega-3-acid ethyl ester may comprise fatty acids, such as eicosapentaenoic acid ethyl ester, docosahexaenoic acid ethyl ester, or combinations thereof. When omega-3-acid ethyl ester is combined with the zwitterionic surfactant in the foaming mixture, the mixture shows a dramatic increase in half-life and decrease in bubble size when compared to a conventional mixture without the omega-3-acid ethyl ester. Such an increase in half-life and a decrease in bubble size are as a result of a synergistic effect between the zwitterionic surfactant and the omega-3-acid ethyl ester. Such an effect correlates with an increase in stability and viscosity of the foaming mixture when introduced to a carbonate reservoir formation.

In embodiments, the omega-3-acid ethyl ester may comprise at least 50 wt. % eicosapentaenoic acid ethyl ester, based on the total weight of the omega-3-acid ethyl ester, with the balance of the omega-3-acid ethyl being docosahexaenoic acid ethyl ester. In other embodiments, the omega-3-acid ethyl ester comprises at least 54 wt. % eicosapentaenoic acid ethyl ester, based on the total weight of the omega-3-acid ethyl ester, with the balance of the omega-3-acid ethyl being docosahexaenoic acid ethyl ester. In specific embodiments, the amount of eicosapentaenoic acid ethyl ester present in the omega-3-acid ethyl ester comprises about 54.8 wt. %, based on the total weight of the omega-3-acid ethyl ester, with the balance of the omega-3-acid ethyl being docosahexaenoic acid ethyl ester.

Suitable ratios of eicosapentaenoic acid ethyl ester to docosahexaenoic acid ethyl ester present in the omega-3-acid ethyl ester may be from 50:50 to 70:30, based on the total weight of the omega-3-acid ethyl ester. Additional suitable ratios of eicosapentaenoic acid ethyl ester to docosahexaenoic acid ethyl ester present in the omega-3-acid ethyl ester may be between 51:49 and 67:43, between 52:48 and 64:46, between 53:47 and 60:40, between 54:46 and 55:45, or from any other suitable ratio between 50:50 and 70:30, based on the total weight of the omega-3-acid ethyl ester.

Referring now to the aqueous salt solution, which is present in the foaming mixture according to certain embodiments. As used in this application, the term "aqueous salt solution" is a general term that refers to various salts and salt mixtures dissolved in an aqueous solution between about 30,000 ppm and 60,000 ppm. Salts present in the aqueous salt solution may include metal salts comprising one or more alkali or alkaline earth metal halides. A non-limiting list of such salts that may be present in the aqueous salt solution may include any salts comprising sodium, chloride, magnesium, potassium, calcium, sulfate, bicarbonate or combinations thereof. Here, the aqueous salt solution is a component of the foaming mixture. The aqueous salt solution may stabilize the foaming mixture upon introducing the foaming mixture to the carbonate reservoir formation.

In certain embodiments, the aqueous salt solution has a salinity of about 57,670 parts per million (ppm) of at least one metal salt. Suitable salinity ranges of salinity may comprise a salinity of less than 60,000 ppm, 55,000 ppm, 50,000 ppm, 45,000 ppm, 40,000 ppm, 35,000 ppm, or 30,000 ppm. Other suitable salinity ranges may comprise a salinity between 30,000 ppm and 60,000 ppm, between 40,000 ppm and 59,000 ppm, between 45,000 ppm and 58,000 ppm, between 50,000 ppm and 57,000 ppm, between 55,000 ppm and 57,000 ppm, or from any other range between 30,000 ppm and 60,000 ppm of at least one metal salt. In any of these embodiments, the aqueous salt solution may be untreated seawater. The untreated seawater may include a concentration ranging from about 3 ppm to 15 ppm of organic material. Such organic materials may include, but are not limited to, dissolved organic carbon (about 1.3 ppm to 6.5 ppm), colloidal organic matter (about 1.3 ppm to 6.5 ppm), detritus (about 0.38 ppm to 1.92 ppm), zooplankton (about 0.039 ppm to 0.195 ppm), bacteria (about 0.012 ppm to 0.060 ppm), phytoplankton (about 0.0012 ppm to 0.0060 ppm), or combinations thereof. An aqueous salt solution with a salinity above 60,000 ppm is undesirable as it may inhibit generation of foam and therefore negatively impact the stability of the foam mixture.

Again referring to the foaming mixture, in some embodiments, the zwitterionic surfactant comprises between 0.1 wt. % and 10.0 wt. % of the foaming mixture, based on the total weight of the foaming mixture. Additional suitable ranges of the zwitterionic surfactant in the foaming mixture may range between 0.2 wt. % and 9.0 wt. %, between 0.3 wt. % and 8.0 wt. %, between 0.4 wt. % and 7.0 wt. %, between 0.5 wt. % and 5.0 wt. %, or from any other suitable range between 0.1 wt. % and 10.0 wt. %, based on the total weight of the foaming mixture. In certain specific embodiments, the zwitterionic surfactant comprises about 0.5 wt. % of the foaming mixture, based on the total weight of the foaming mixture.

In additional embodiments, the omega-3-acid ethyl ester comprises between 5.0 wt. % and 15.0 wt. % of the foaming mixture, based on the total weight of the foaming mixture. Additional suitable ranges of the omega-3-acid ethyl ester in the foaming mixture may range between 6.0 wt. % and 14.0 wt. %, between 7.0 wt. % and 13.0 wt. %, between 8.0 wt. % and 12.0 wt. %, between 9.0 wt. % and 11.0 wt. %, or from any other suitable range between 5.0 wt. % and 15.0 wt. %, based on the total weight of the foaming mixture. In certain embodiments, the omega-3-acid ethyl ester comprises about 5.0 wt. % of the foaming mixture, based on the total weight of the foaming mixture.

In further embodiments, the aqueous salt solution comprises between 75.0 wt. % and 95.0 wt. % of the foaming mixture, based on the total weight of the foaming mixture. Additional suitable ranges of the aqueous salt solution in the foaming mixture may range between 80.0 wt. % and 95.0 wt. %, between 82.0 wt. % and 95.0 wt. %, between 84.0 wt. % and 95.0 wt. %, between 86.0 wt. % and 95.0 wt. %, between 88.0 wt. % and 95.0 wt. %, between 90.0 wt. % and 95.0 wt. %, between 92.0 wt. % and 95.0 wt. % or from any other suitable range between 80.0 wt. % and 95.0 wt. %, based on the total weight of the foaming mixture. In certain specific embodiments, the aqueous salt solution comprises about 95.0 wt. % of the foaming mixture, based on the total weight of the foaming mixture.

Referring again to the foaming mixture, the foaming mixture may have a temperature of greater than about 10 degrees Celsius (° C.). Other suitable temperature ranges may include a temperature of greater than 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C. Additional suitable temperature ranges may include a temperature ranging between 30° C. and 100° C., between 40° C. and 100° C., between 50° C. and 100° C., between 60° C. and 100° C., between 70° C. and 100° C., between 75° C. and 100° C., between 80° C. and 100° C., between 85° C. and 100° C., between 90° C. and 100° C., or from any other range between 30° C. and 100° C.

In some embodiments, the foaming mixture may have a pH ranging between 6.0 and 9.5. Other suitable pH ranges may comprise a pH ranging between 6.0 and 9.0, between 6.5 and 9.5, between 6.5 and 9.0, between 7.0 and 9.0, between 7.0 and 8.5, between 7.5 and 9.0, between 7.5 and 8.5, or from any other range between 6.0 and 9.5.

Thus, various embodiments of the foaming mixture have been described. Embodiments of methods for enhancing hydrocarbon recovery in a carbonate reservoir formation will now be described. The methods may include the foaming mixture according to any of the embodiments previously described.

In embodiments, a method for enhancing hydrocarbon recovery in a carbonate reservoir formation includes introducing a foaming mixture to the carbonate reservoir formation such that any hydrocarbon present in the carbonate reservoir formation is displaced by the foaming mixture and is recoverable from the carbonate reservoir formation. The foaming mixture may comprise a zwitterionic surfactant, an omega-3-acid ethyl ester, and aqueous salt solution; and the omega-3-acid ethyl ester is selected from the group comprising eicosapentaenoic acid ethyl ester, docosahexaenoic acid ethyl ester, or combinations thereof.

In certain embodiments, the method for enhancing hydrocarbon recovery in a carbonate reservoir formation further includes injecting an amount of carbon dioxide to the carbonate reservoir formation. Carbon dioxide ($CO_2$) is a vital component for generating foam in a carbonate reservoir formation, as generating foam may require a gas phase, a liquid phase (that is, the foaming mixture), and a shearing force. The shearing force may be provided by reservoir rock pores and an injection pressure of the $CO_2$. The $CO_2$ allows the gas phase to mix with the liquid phase. When the liquid phase and the gas phase are injected into the carbonate reservoir formation, in situ foam generation occurs. The injection of carbon dioxide to the carbonate reservoir formation may occur simultaneously or after introducing the foaming mixture to the carbonate reservoir formation.

EXAMPLES

The following examples illustrate one or more additional features of the present disclosure described previously.

In the following examples, various foaming mixtures were prepared and tested for their suitability of enhancing hydrocarbon recovery in a carbonate reservoir formation.

Generally, the comparative foaming mixture was prepared by combining 0.167 grams (g) of the zwitterionic surfactant according to one or more embodiments presently described with 9.333 g of the aqueous salt solution at 24° C. in a test tube. The aqueous salt solution of the comparative foaming mixture was untreated seawater with a salinity of about 57,670 ppm from the Quarraya Sea. The comparative foaming mixture was then shaken in bulk test for one minute with constant shearing stress for one minute and the height of the foam recorded every hour for 24 hours.

The bulk tests were used as the method for testing the ability of the comparative foaming mixture and the experimental foaming mixture to produce foam and stability of the foam after it was generated. Bulk tests were performed by filling the test tube and then shaking the test tube by hand for an amount of time with fixed amounts of strength to achieve approximate consistency.

The experimental foaming mixture was prepared by combining 0.167 g of the zwitterionic surfactant, 0.500 g of the omega-3-acid ethyl ester, and 9.333 g of the aqueous salt solution at 24° C. in a test tube. The zwitterionic surfactant is commercially available from Schlumberger Ltd.® as Methanol Surfactant Foamer F107®. The omega-3-acid ethyl ester comprised 54.8 wt. % eicosapentaenoic acid ethyl ester and 45.2 wt. % docosahexaenoic acid ethyl ester, based on the total weight of the omega-3-acid ethyl ester. Again, the aqueous salt solution was untreated seawater with a salinity of about 57,670 ppm from the Quarraya Sea. The foaming mixture was then shaken in bulk test with constant sheering stress for one minute and the height of the foam recorded every hour for 24 hours.

TABLE 1

Foam Height of the Experimental Foaming Mixture vs. the Comparative Foaming Mixture

| Foam height (cm) | | |
| --- | --- | --- |
| Comparative Foaming Mixture | Experimental Foaming Mixture | Duration (hours) |
| 9.30 | 10.00 | 1 |
| 5.15 | 8.50 | 2 |
| 2.95 | 8.15 | 3 |
| 2.00 | 6.75 | 4 |

As can be seen in Table 1 and FIG. 1, the foam half-life of the experimental foaming mixture was significantly improved when compared to the comparative foaming mixture. The foam half-life of the foaming mixture is considered an indicative way of quantifying the strength, stability, and viscosity of the foam. The experimental foaming mixture showed a noticeably improved foam height with a half-life that was at least three times longer than the comparative foaming mixture. More specifically, it took only about 2.1 hours for the comparative foaming mixture to reach its half-life. In contrast, the experimental foaming mixture took about 6.5 hours to reach its half-life. These results indicate a much improved half-life for the experimental foaming mixture, which shows its suitability as strong, stable, and viscous foam for enhancing hydrocarbon recovery in a carbonate reservoir formation.

While not shown in FIG. 1, the experimental foaming mixtures, even at lower concentrations of omega-3-acid ethyl ester, showed improved foam height and half-life when compared to the comparative foaming mixture. These results indicate that there are synergistic properties in the foaming mixture between the omega-3-acid ethyl ester and the zwitterionic surfactant that enhance hydrocarbon recovery in a carbonate reservoir formation during EOR.

It is also noted that recitations of "at least one" component or element should not be used to create an inference that the alternative use of the articles "a" or "an" should be limited to a single component or element.

It is noted that terms like "typically," when utilized in this application, are not utilized to limit the scope of the claimed subject matter or to imply that certain features are critical, essential, or even important to the structure or function of the claimed subject matter. Rather, these terms are merely intended to identify particular aspects of an embodiment of the present disclosure or to emphasize alternative or additional features that may or may not be utilized in a particular embodiment of the present disclosure.

It is noted that one or more of the following claims utilize the term "in which" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used preamble term "wherein."

For the purposes of describing and defining the present technology it is noted that the term "about" is utilized in this application to represent the inherent degree of uncertainty that may be attributed to any quantitative comparison, value, measurement, or other representation. The term "about" is also utilized in this application to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed in this application should not be taken to imply that these details relate to elements that are essential components of the various embodiments described in this application, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified in this application as preferred or particularly advantageous, it is contemplated that the present disclosure is not necessarily limited to these aspects.

According to a first aspect of the present disclosure, a method for enhancing hydrocarbon recovery in a carbonate reservoir formation includes introducing a foaming mixture to the carbonate reservoir formation such that any hydrocarbon present in the carbonate reservoir formation is displaced by the foaming mixture and is recoverable from the carbonate reservoir formation. The foaming mixture may comprise a zwitterionic surfactant, an omega-3-acid ethyl ester, and aqueous salt solution; and the omega-3-acid ethyl ester is selected from the group comprising eicosapentaenoic acid ethyl ester, docosahexaenoic acid ethyl ester, or combinations thereof.

A second aspect of the present disclosure may include the first aspect, in which the zwitterionic surfactant is selected from lauramine oxide, cocamine oxide, cocamidopropyl betaine, myristamine oxide, or combinations thereof.

A third aspect of the present disclosure may include the first aspect or second aspect, in which the lauramine oxide, cocamine oxide, cocamidopropyl betaine, myristamine oxide, or combinations thereof comprise between 15 wt. % and 40 wt. % of the zwitterionic surfactant.

A fourth aspect of the present disclosure may include any of the first through third aspects, in which the zwitterionic surfactant further comprises an alcohol.

A fifth aspect of the present disclosure may include any of the first through fourth aspects, in which the alcohol is at least one primary alcohol or at least one secondary alcohol, in which the at least one primary alcohol or the at least one secondary alcohol comprises between one and six carbon atoms.

A sixth aspect of the present disclosure may include any of the first through fifth aspects, in which the alcohol comprises isopropanol.

A seventh aspect of the present disclosure may include any of the first through sixth aspects, in which the alcohol comprises between 10 wt. % and 30 wt. % of the zwitterionic surfactant.

An eighth aspect of the present disclosure may include any of the first through seventh aspects, in which the omega-3-acid ethyl ester comprises at least 50 wt. % eicosapentaenoic acid ethyl ester with the balance being docosahexaenoic acid ethyl ester.

A ninth aspect of the present disclosure may include any of the first through eighth aspects, in which the foaming mixture has a pH ranging between 6.0 and 9.5.

A tenth aspect of the present disclosure may include any of the first through ninth aspects, in which the foaming mixture comprises between 0.1 wt. % and 10.0 wt. % of zwitterionic surfactant, between 5.0 wt. % and 15 wt. % of the omega-3-acid ethyl ester, and between 75 wt. % and 95 wt. % aqueous salt solution.

An eleventh aspect of the present disclosure may include any of the first through tenth aspects, in which the aqueous salt solution has a salinity ranging between 50,000 ppm and 75,000 ppm of at least one metal salt.

A twelfth aspect of the present disclosure may include any of the first through eleventh aspects, in which the at least one metal salt comprises one or more alkali or alkaline earth metal halides.

A thirteenth aspect of the present disclosure may include any of the first through twelfth aspects, in which the aqueous salt solution comprises seawater.

A fourteenth aspect of the present disclosure may include any of the first through thirteenth aspects, in which the method for enhancing hydrocarbon recovery in a carbonate reservoir formation further includes injecting an amount of carbon dioxide to the carbonate reservoir formation.

According to a fifteenth aspect of the present disclosure, a zwitterionic surfactant may include an omega-3-acid ethyl ester, and aqueous salt solution, in which the omega-3-acid ethyl ester comprises eicosapentaenoic acid ethyl ester and docosahexaenoic acid ethyl ester.

A sixteenth aspect of the present disclosure may include the fifteenth aspect, in which the zwitterionic surfactant is selected from lauramine oxide, cocamine oxide, cocamidopropyl betaine, myristamine oxide, or combinations thereof.

A seventeenth aspect of the present disclosure may include the fifteenth aspect or sixteenth aspect, in which the zwitterionic surfactant further comprises an alcohol.

An eighteenth aspect of the present disclosure may include any of the fifteenth through seventeenth aspects, in which the omega-3-acid ethyl ester comprises at least 50 wt. % eicosapentaenoic acid ethyl ester with the balance being docosahexaenoic acid ethyl ester.

A nineteenth aspect of the present disclosure may include any of the fifteenth through eighteenth aspects, in which the foaming mixture has a pH ranging between 6.0 and 9.5.

A twentieth aspect of the present disclosure may include any of the fifteenth through nineteenth aspects, in which the foaming mixture comprises between 0.5 wt. % and 10 wt. % of zwitterionic surfactant, between 5.0 wt. % and 15 wt. % of the omega-3-acid ethyl ester, and between 75 wt. % and 95 wt. % aqueous salt solution.

According to a twenty first aspect of the present disclosure, a method for enhancing hydrocarbon recovery in a carbonate reservoir formation includes mixing a zwitterionic surfactant, an omega-3-acid ethyl ester, and aqueous salt solution to produce a foaming mixture; and introducing the foaming mixture to the carbonate reservoir formation such that hydrocarbon present in a carbonate reservoir formation is displaced by the foaming mixture to thereby recover hydrocarbon from the carbonate reservoir formation.

What is claimed is:

1. A method for enhancing hydrocarbon recovery in a carbonate reservoir formation, the method comprising:
   introducing a foaming mixture to the carbonate reservoir formation such that hydrocarbon present in the carbonate reservoir formation is displaced by the foaming mixture and is recoverable from the carbonate reservoir formation, where
      the foaming mixture comprises a zwitterionic surfactant, an omega-3-acid ethyl ester, and aqueous salt solution; and
      the omega-3-acid ethyl ester is selected from the group consisting of eicosapentaenoic acid ethyl ester, docosahexaenoic acid ethyl ester, or combinations thereof.

2. The method of claim 1, in which the zwitterionic surfactant comprises lauramine oxide, cocamine oxide, cocamidopropyl betaine, myristamine oxide, or combinations thereof.

3. The method of claim 2, in which the lauramine oxide, cocamine oxide, cocamidopropyl betaine, myristamine oxide, or combinations thereof comprise between 15 wt. % and 40 wt. % of the zwitterionic surfactant.

4. The method of claim 1, in which the zwitterionic surfactant further comprises an alcohol.

5. The method of claim 4, in which the alcohol is at least one primary alcohol or at least one secondary alcohol, in which the at least one primary alcohol or the at least one secondary alcohol comprises between one and six carbon atoms.

6. The method of claim 4, in which the alcohol comprises isopropanol.

7. The method of claim 4, in which the alcohol comprises between 10 wt. % and 30 wt. % of the zwitterionic surfactant.

8. The method of claim 1, in which the omega-3-acid ethyl ester comprises at least 50 wt. % eicosapentaenoic acid ethyl ester with the balance being docosahexaenoic acid ethyl ester.

9. The method of claim 1, in which the foaming mixture has a pH ranging between 6.0 and 9.5.

10. The method of claim 1, in which the foaming mixture comprises between 0.1 wt. % and 10.0 wt. % of zwitterionic surfactant, between 5.0 wt. % and 15 wt. % of the omega-3-acid ethyl ester, and between 75 wt. % and 95 wt. % aqueous salt solution.

11. The method of claim 1, in which the aqueous salt solution has a salinity ranging between 50,000 ppm and 75,000 ppm of at least one metal salt.

12. The method of claim 11, in which the at least one metal salt comprises one or more alkali or alkaline earth metal halides.

13. The method of claim 1, in which the method for enhancing hydrocarbon recovery in a carbonate reservoir formation further includes injecting an amount of carbon dioxide into the carbonate reservoir formation.

* * * * *